US012029617B2

(12) United States Patent
Wang et al.

(10) Patent No.: US 12,029,617 B2
(45) Date of Patent: Jul. 9, 2024

(54) DEVICE TO REDUCE STEAM POPS AND INCREASE TISSUE STABILITY DURING RADIOFREQUENCY ABLATION

(71) Applicant: Avent, Inc., Alpharetta, GA (US)

(72) Inventors: Ruoya Wang, Decatur, GA (US); Rasagnya M. Viswanadha, Cumming, GA (US); Jennifer J. Barrett, Alpharetta, GA (US); Tyler W. Crone, Atlanta, GA (US); Joseph DiPietro, Ponte Verde, FL (US); Kun-Chi Wu, Johns Creek, GA (US)

(73) Assignee: Avent, Inc., Alpharetta, GA (US)

( * ) Notice: Subject to any disclaimer, the term of this patent is extended or adjusted under 35 U.S.C. 154(b) by 1148 days.

(21) Appl. No.: 16/620,625

(22) PCT Filed: Jun. 14, 2018

(86) PCT No.: PCT/US2018/037515
§ 371 (c)(1),
(2) Date: Dec. 9, 2019

(87) PCT Pub. No.: WO2018/232106
PCT Pub. Date: Dec. 20, 2018

(65) Prior Publication Data
US 2020/0188054 A1  Jun. 18, 2020

Related U.S. Application Data

(60) Provisional application No. 62/520,179, filed on Jun. 15, 2017.

(51) Int. Cl.
*A61B 90/00* (2016.01)
*A61B 18/00* (2006.01)
(Continued)

(52) U.S. Cl.
CPC .......... *A61B 90/04* (2016.02); *A61B 18/1206* (2013.01); *A61B 18/14* (2013.01);
(Continued)

(58) Field of Classification Search
CPC ..... A61B 90/04; A61B 18/1206; A61B 18/14; A61B 90/18; A61B 2018/00577;
(Continued)

(56) References Cited

U.S. PATENT DOCUMENTS 4,116,236 A   9/1978  Albert
4,981,142 A   1/1991  Dachman
(Continued)

FOREIGN PATENT DOCUMENTS

CA   2764470 A1 * 12/2010  .......... A61F 13/062
DE   3511250 A1   11/1985
(Continued)

OTHER PUBLICATIONS

International Search Report and Written Opinion for PCT/US2018/037515, dated Sep. 28, 2018, 13 pages.
(Continued)

*Primary Examiner* — Tarla R Patel
(74) *Attorney, Agent, or Firm* — Meunier Carlin & Curfman LLC (57) ABSTRACT

The present invention is directed to a system for delivering radiofrequency ablation energy to an area or volume of tissue. The system includes a wrap, where a stiffening element surrounds an opening in the wrap, where the stiffening element transfers radial compression to the area or volume of tissue, where the radial compression increases stability of the area or volume of tissue; and at least one radiofrequency ablation probe having an active electrode, where the at least one radiofrequency ablation probe is connected to a radiofrequency generator via a lead. A device
(Continued)

that includes a wrap and a method of delivering radiofrequency ablation energy to a volume of tissue via the device are also described.

11 Claims, 6 Drawing Sheets (51) Int. Cl.
*A61B 18/12* (2006.01)
*A61B 18/14* (2006.01)
*A61B 90/18* (2016.01)
*A61F 5/01* (2006.01)

(52) U.S. Cl.
CPC .... *A61B 90/18* (2016.02); *A61B 2018/00577* (2013.01); *A61B 2018/00821* (2013.01); *A61B 2090/0409* (2016.02); *A61B 2090/3966* (2016.02); *A61F 5/0106* (2013.01)

(58) Field of Classification Search
CPC .. A61B 2018/00821; A61B 2090/0409; A61B 2090/3966; A61B 18/1402; A61B 18/12; A61F 5/0106; A61F 5/0109; A61F 2005/0176; A61F 5/30
See application file for complete search history.

(56) References Cited

U.S. PATENT DOCUMENTS

| | | | |
|---|---|---|---|
| 5,462,521 A | 10/1995 | Brucker et al. | |
| 5,692,520 A | 12/1997 | Lavoisier | |
| 5,947,913 A * | 9/1999 | Palumbo | A61N 1/36003 |
| | | | 602/2 |
| 6,053,937 A | 4/2000 | Edwards et al. | |
| 6,129,695 A * | 10/2000 | Peters | A61F 5/0109 |
| | | | 602/61 |
| 6,210,406 B1 | 4/2001 | Webster | |
| 6,752,804 B2 | 6/2004 | Simpson et al. | |
| 9,023,030 B2 | 5/2015 | Koblish et al. | |
| 9,119,636 B2 | 9/2015 | Vegesna et al. | |
| 9,149,330 B2 | 10/2015 | Sharareh et al. | |
| 9,358,064 B2 | 6/2016 | Clark, III et al. | |
| 9,393,068 B1 | 7/2016 | Leo et al. | |
| 9,474,574 B2 | 10/2016 | Ibrahim et al. | |
| 2004/0134501 A1* | 7/2004 | Hargis | A61F 5/0109 |
| | | | 128/882 |
| 2005/0038367 A1* | 2/2005 | McCormick | A61F 5/0106 |
| | | | 602/26 |
| 2007/0055225 A1* | 3/2007 | Dodd, III | A61B 18/14 |
| | | | 606/34 |
| 2010/0168620 A1 | 7/2010 | Klimovitch et al. | |
| 2011/0224667 A1 | 9/2011 | Koblish et al. | |
| 2011/0282190 A1* | 11/2011 | Caffey | A61B 5/0066 |
| | | | 600/427 |
| 2012/0123411 A1 | 5/2012 | Ibrahim et al. | |
| 2012/0165669 A1 | 6/2012 | Barley et al. | |
| 2013/0072837 A1* | 3/2013 | Rousso | A61H 11/02 |
| | | | 601/152 |
| 2014/0066917 A1 | 3/2014 | Cosman, Jr. et al. | |
| 2014/0309567 A1 | 10/2014 | Wright et al. | |
| 2015/0150629 A1 | 6/2015 | Anderson et al. | |
| 2016/0354091 A1 | 12/2016 | Saatchi et al. | |

FOREIGN PATENT DOCUMENTS

| | | | | |
|---|---|---|---|---|
| EP | 2788078 B1 * | 9/2020 | | A61B 17/00 |
| FR | 2532839 A1 | 3/1984 | | |
| JP | 3159593 U | 5/2010 | | |
| JP | 2011131061 A | 7/2011 | | |
| JP | 2016510643 T | 4/2016 | | |
| WO | WO 2005/007045 A1 | 1/2005 | | |
| WO | WO-2005007045 A1 * | 1/2005 | | A61F 13/062 |
| WO | WO-2005097020 A1 * | 10/2005 | | A61F 13/02 |
| WO | 2007/056734 A1 | 5/2007 | | |
| WO | WO-2012106371 A1 * | 8/2012 | | A61B 18/042 |
| WO | WO-2015073397 A1 * | 5/2015 | | A61B 17/3417 |
| WO | 2016/032931 A | 3/2016 | | |
| WO | WO-2018183002 A1 * | 10/2018 | | A61B 17/1615 |

OTHER PUBLICATIONS

Communication pursuant to Article 94(3) EPC issued in corresponding EP Application No. 18737121.6 dated Mar. 2, 2023.

* cited by examiner

DEVICE TO REDUCE STEAM POPS AND INCREASE TISSUE STABILITY DURING RADIOFREQUENCY ABLATION

CROSS REFERENCE TO RELATED APPLICATIONS

The present application is the national stage entry of International Patent Application No. PCT/US2018/037515, having a filing date of Jun. 14, 2018, which claims priority to U.S. Provisional Patent Application Ser. No. 62/520,179, having a filing date of Jun. 15, 2017, both of which are incorporated herein by reference for all purposes.

FIELD OF THE INVENTION

The present invention relates generally to a system for increasing tissue stability and reducing steam pops during radiofrequency ablation.

BACKGROUND OF THE INVENTION

Radiofrequency ablation devices are used for the treatment of chronic pain by ablating or lesioning nerve tissue that is the source of a patient's pain. Cooled radiofrequency devices have been used to create a lesion of greater volume. The increase in lesion volume can increase the probability and clinical success of ablating the target nerve tissue. Cooled radiofrequency ablation is achieved by delivering cooling fluid (e.g., sterile water) via a peristaltic pump through an active electrode on a radiofrequency ablation probe in a closed-loop circulation. The circulating cooling fluid transfers heat away from the active electrode located on the radiofrequency ablation probe, allowing the electrode-tissue interface temperature to be maintained at a level so as to not increase the temperature of the tissue close to the boiling point of water resulting in charring or dehydration or significant desiccation of the surrounding tissue. Thus, more energy can be delivered to the lesion site, resulting in the creation of a larger lesion volume compared to conventional radiofrequency ablation methods that do not include such cooling.

The effectiveness of energy delivery from the active electrode to the tissue to be lesioned is highly dependent on the contact surface area and the force at the probe-tissue interface. For probes with temperature control, the thermocouple-tissue contact properties are important. For instance, lack of regulation or control over the amount of probe-tissue contact can result in localized heating, decreased temperature feedback sensitivity, and increased power demand by the probe. Further, if the local tissue temperature exceeds 100° C., an audible sound produced when steam gas escapes the lesion site, known as a "steam pop," can occur, where the pressure build-up and sudden release of steam can result in erratic temperature and power behaviors.

As such, a need exists for a radiofrequency ablation system, device, and method that can stabilize the lesion site to limit the control of steam pops, which would result in increased patient and user satisfaction, more consistent clinical outcomes, and decreased procedural delay due to poor feedback control.

SUMMARY OF THE INVENTION

Objects and advantages of the invention will be set forth in part in the following description, or may be obvious from the description, or may be learned through practice of the invention.

According to one embodiment of the present invention, a device for providing radial compression to a volume of tissue surrounding an active electrode of a radiofrequency ablation probe during the delivery of radiofrequency ablation energy to the volume of tissue is provided. The device includes a wrap, where a stiffening element (which may be radiopaque) surrounds an opening in the wrap, where the stiffening element transfers radial compression to the volume of tissue, and where the radial compression increases stability of the volume of tissue.

In another embodiment, the wrap can include an elastic material.

In yet another embodiment of the invention, at least a portion of the stiffening element on the compression device may be radiopaque.

In still another embodiment, the opening can facilitate the insertion of the active electrode of the radiofrequency ablation probe into the volume of tissue.

In one more embodiment, the transfer of radial compression to the volume of tissue can improve contact between the volume of tissue and the active electrode of the radiofrequency ablation probe.

In yet another embodiment, the wrap can facilitate immobilization of the volume of tissue, where the wrap can be adjustable to accommodate limb (e.g., knee) diameters ranging from about 8 inches (20.32 centimeters) to about 40 inches (101.6 centimeters). Further, the volume of tissue can be located at a knee of a patient, where a bend in the knee of the patient can be maintained at an angle ranging from about 70° to about 180° (e.g., from 80° to 175° or from 90° to 170°. It is contemplated that the volume of tissue may be located at other large joints (e.g., hip, shoulder, elbow, etc.) or smaller joints (e.g., wrist, ankle, finger, toe or the like) during the delivery of radiofrequency ablation energy.

In one more embodiment, the wrap can include fastening means. For example, the fastening means can include hooks and loops, compression straps, tape, buttons, snaps, or a combination thereof.

According to another embodiment of the present invention, a system for delivering radiofrequency ablation energy to a volume of tissue is provided. The system includes a wrap, where a stiffening element surrounds an opening in the wrap, where the stiffening element transfers radial compression to the volume of tissue, where the radial compression increases stability of the volume of tissue; and a radiofrequency ablation probe having an active electrode, where the radiofrequency ablation probe is connected to a radiofrequency generator via a lead or cable.

In one particular embodiment, the wrap can include an elastic material and a fastening means. Further, at least a portion of the stiffening element can include a radiopaque material.

In another embodiment, the opening can facilitate the insertion of the active electrode of the radiofrequency ablation probe into the volume of tissue.

In still another embodiment, the transfer of radial compression to the volume of tissue can improve contact between the volume of tissue and the active electrode of the radiofrequency ablation probe.

In yet another embodiment, the wrap can facilitate immobilization of the volume of tissue, where the wrap can be adjustable to accommodate limb (e.g., knee) diameters ranging from about 8 inches (20.32 centimeters) to about 40 inches (101.6 centimeters). Further, the volume of tissue can be located at a knee of a patient, where a bend in the knee of the patient can be maintained at an angle ranging from about 70° to 180° (e.g., from about 80° to 175° or from about 90° to about 170°.

In one more embodiment, the radiofrequency ablation probe can include a radiopaque marker adjacent the active electrode.

According to one more embodiment of the present invention, a method of delivering radiofrequency ablation energy to a volume of tissue is provided. The method includes: providing radial compression to the volume of tissue utilizing a device, where the device is secured about the volume of tissue, where the device comprises a wrap, where a stiffening element (which may be radiopaque) surrounds an opening in the wrap; inserting a radiofrequency ablation probe having an active electrode into the volume of tissue through the opening; and delivering energy to the volume of tissue through the active electrode of the radiofrequency ablation probe to form a lesion, where the radial compression reduces gas buildup at the lesion.

In another embodiment, the stiffening element can transfer radial compression to the volume of tissue, where the radial compression can increase stability of the volume of tissue.

In still another embodiment, the device can be secured about the volume of tissue via fastening means.

In yet another embodiment, the volume of tissue can be immobilized by the wrap, where the wrap can be adjustable to accommodate limb (e.g., knee) diameters ranging from about 8 inches (20.32 centimeters) to about 40 inches (101.6 centimeters).

In one more embodiment, the volume of tissue can be located at a knee of a patient, where a bend in the knee of the patient can be maintained at an angle ranging from about 70° to 180° (e.g., from about 80° to 175°, from about 90° to about 170°.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention to one skilled in the art, including the best mode thereof, is set forth more particularly in the remainder of the specification, including reference to the accompanying figures, in which.

Repeat use of reference characters in the present specification and drawings is intended to represent the same or analogous features or elements of the present invention.

DETAILED DESCRIPTION OF THE INVENTION

Reference will now be made in detail to embodiments of the present invention, examples of which are illustrated in the figures. Each embodiment is provided by way of explanation of the invention and is not meant as a limitation of the invention. For example, features illustrated or described as part of one embodiment may be used with another embodiment to yield still a further embodiment. It is intended that the present invention include these and other modifications and variations coming within the scope and spirit of the invention.

Generally speaking, the present invention is directed to a device to increase tissue stability and reduce the occurrence of steam pops during radiofrequency ablation by facilitating the application of radial compression to an area or volume of tissue during the delivery of radiofrequency ablation energy to the area or volume of tissue, wherein the device comprises a wrap, wherein a stiffening element (which may be radiopaque) surrounds an opening in the wrap, wherein the stiffening element transfers radial compression to the area or volume of tissue, wherein the radial compression increases stability of the area or volume of tissue stability of the volume of tissue and increases contact quality between the active electrode and tissue. For instance, when a radiofrequency ablation probe is inserted into the area or volume of tissue, the device can compress the area or volume of tissue around the active electrode (e.g., the active tip) of the radiofrequency ablation probe, thus directly improving the contact properties between the probe and the area or volume of tissue, as well as the temperature feedback. In other words, as a lesion is formed by the radiofrequency ablation probe, elastic tension in the device can be transferred into a compressive force localized around the lesion or area/volume of tissue, resulting in a greater likelihood of increased contact area and force between the active electrode (e.g., the active tip) and the thermocouple components of the radiofrequency ablation probe and the tissue, allowing for better temperature feedback control and delivery of the radiofrequency energy. In addition, the radial compression can reduce gas buildup at the area or volume of tissue, which, in turn, reduces the occurrence of steam pops during the delivery of radiofrequency ablation energy to the area or volume of tissue. The device can also immobilize a joint near the area or volume of tissue to be ablated and can maintain the joint at a desired angle, where such immobilization also improves the delivery of the radiofrequency energy.

Figure 1:
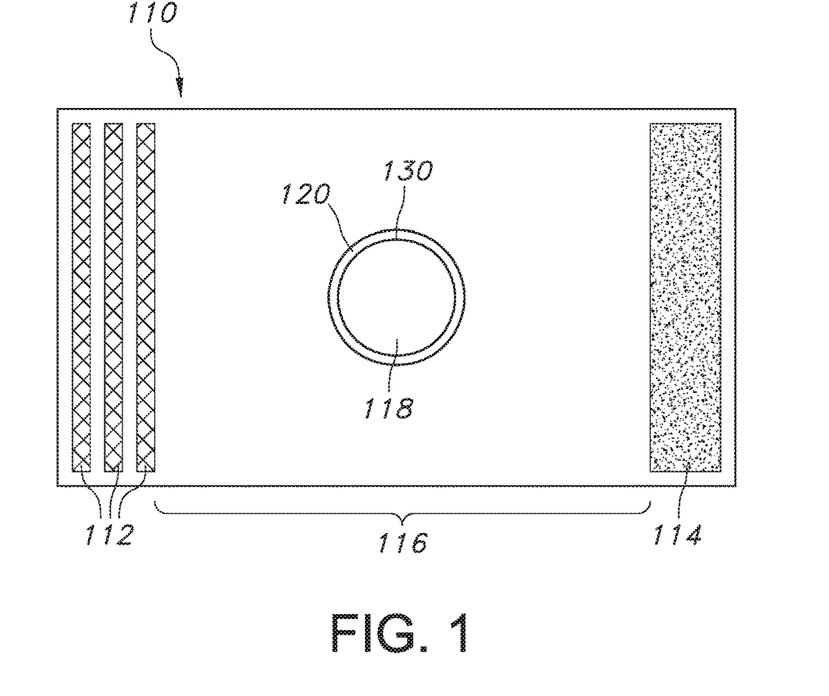
FIG. 1 is a front view of one embodiment of a tissue stability device as contemplated by the present invention.

Referring now to FIG. 1, one embodiment of a device 110 contemplated by the present invention is shown. The device 110 can be in the form of a wrap, band, brace, etc. that has an elastic portion 116. The elastic portion 116 can be formed from any suitable elastic material. For example, the elastic portion 116 can be formed from any suitable elastic materials. Suitable elastic materials may include, but are not limited to, elastic nonwoven fabrics, elastic films, knit fabrics having stretch and recovery properties (e.g., imparted by use of elastic threads/filaments such as, for example, LYCRA brand threads/filaments), woven fabrics having stretch and recovery properties (e.g., imparted by use of elastic threads/filaments such as, for example, LYCRA brand threads/filaments), laminates of non-elastic and elastic materials such that the resulting laminates have stretch and recovery properties. Exemplary elastomeric materials include stretch-bonded-laminate (SBL) materials (See for example, U.S. Pat. No. 4,720,415 issued Jan. 19, 1988 to Vander Wielen et al.), neck-bonded-laminate (NBL) materials (See for example, U.S. Pat. No. 5,226,992 issued Jul. 13, 1992 to Morman), elastomeric films, elastomeric foam materials, or the like, which are elastomerically stretchable and have recovery properties along at least one direction.

Further, the device 110 can be adjustable to accommodate limb (e.g., knee) diameters ranging from about 8 inches (20.32 centimeters) to about 40 inches (101.6 centimeters). In this respect, the device 110 (e.g., wrap) can have a universal size ranging from about 8 inches (20.32 centimeters) to about 40 inches (101.6 centimeters). In another embodiment, the device 110 (e.g., wrap) can be available in various sizes. For instance, the device 110 can be available in sizes small, medium, and large, where the size small device can accommodate limb (e.g., knee) diameters ranging from about 8 inches (20.32 centimeters) to about 14 inches (35.56 centimeters), the size medium device can accommodate limb (e.g., knee) diameters ranging from about 14 inches (35.56 centimeters) to about 25 inches (63.5 centimeters), and the size large device can accommodate limb (e.g., knee) diameters ranging from about 25 inches (63.5 centimeters) to about 40 inches (101.6 centimeters).

The device 110 can also include fastening means. Although any suitable fastening means can be used, such as snaps, adhesives, etc., the fastening means can, in some embodiments, be in the form of hooks 112 and loops 114. However, it is also to be understood that any other suitable fastening means can be utilized, such as compression straps, tape, buttons, snaps, or a combination thereof. The fastening means can ensure that the device 110 is sufficiently secure to stabilize the area or volume of tissue that is being treated with radiofrequency ablation. For instance, the presence of multiple sections of hooks 112 disposed along an end of the wrap, band, brace, etc. allows for the device 110 to be secured about the patient's body or an appendage (elbow, arm, knee, leg, etc.) so that the optima elastic tension can be achieved to stabilize the area or volume of tissue 128 that is being treated. The device 110 can also include at least one opening 118, where the opening 118 facilitates the delivery of radiofrequency ablation energy to the area or volume of tissue via a probe, as discussed in more detail with respect to FIGS. 2 and 3.

Further, a stiffening element 120 can surround the opening 118, where the stiffening element 120 can help to transfer radial compression to the area or volume of tissue 128 that is being treated, which can increase tissue stability at the ablation site. The stiffening element 120 can be formed from a rigid ring of a plastic material, a metal material, or a composite material and can be disposed on a surface of the device 110. Rigid or semi-rigid foams, rigid or semi-rigid papers and/or paperboards (coated or uncoated), inflatable structures that can be pressurized until the desired structure is achieved, thicker and stiffened regions of the fabric or material used to form the device (can be stiffened with glues or adhesives), electro-viscous materials, phase change materials and combinations thereof. The stiffening element 120 (whether or not in the form of a rigid ring) may be radiopaque. By making the stiffening element radiopaque, it is generally believed to make it easier to co-locate the probe after placement relative to the compression device. Any suitable radiopaque materials can be used to render all (or only one or more portions) of the stiffening element radiopaque. An example of a suitable radiopaque material that may be used to impart the desired radiopacity is radiopaque ink with tungsten that is pad printed onto the stiffening element. Other suitable materials include, but are not limited to, high density metals such as platinum, iridium, gold, silver, tantalum or their alloys, or radiopaque polymeric compounds and/or powders that may be coated onto or otherwise formulated into the material of the stiffening element. Such materials are highly visible under fluoroscopic illumination and are therefore visible even at minimal thicknesses. Regardless of the radiopaque marker(s) or materials utilized on the stiffening element, the stiffening element can be used in conjunction with an x-ray, fluoroscopy, or ultrasound device in order to help visualize and co-locate a probe (desirably a radiopaque probe) during insertion of the probe into the volume of tissue.

Figure 2:
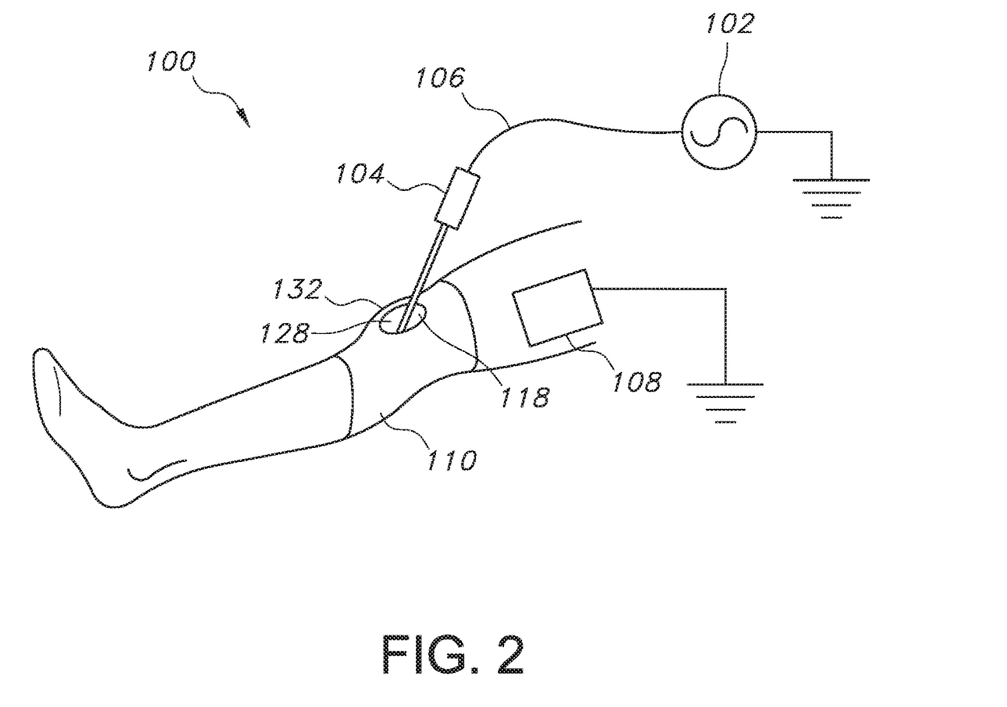
FIG. 2 is a perspective view of one embodiment of a radiofrequency ablation system contemplated by the present invention, where the system includes the device of FIG. 1

As shown in FIG. 2, the device 110 of FIG. 1 can be part of a radiofrequency ablation system 100. In addition to the device 110, the system 100 can include a signal or pulse generator (e.g., radiofrequency generator) 102 connected to a radiofrequency ablation probe 104 via a lead 106, as well as a ground pad 108, which can be secured to a patient. In one particular embodiment, the system 100 can be used to delivery radiofrequency ablation energy to an area or volume of tissue 128 near a patient's knee 132. When the device 110 is secured about the patient's knee, for instance, the opening 118 in the device 110 allows for the radiofrequency ablation probe 104 to be inserted to a desired area or volume of tissue 128 to deliver radiofrequency ablation energy to form a lesion 126 (see FIG. 3) at the area or volume of tissue 128. Moreover, although FIGS. 1 and 2 show a device 110 with one opening 118, it is to be understood that one or more openings 118 can be included in the device 110 for the insertion of one or more radiofrequency ablation probes 104 into an area of volume of tissue 128. For instance, the device 110 can include two openings 118 for receiving two radiofrequency ablation probes 104. Alternatively, the device 110 can include one opening 118 for receiving two radiofrequency ablation probes 104.

Figure 3:
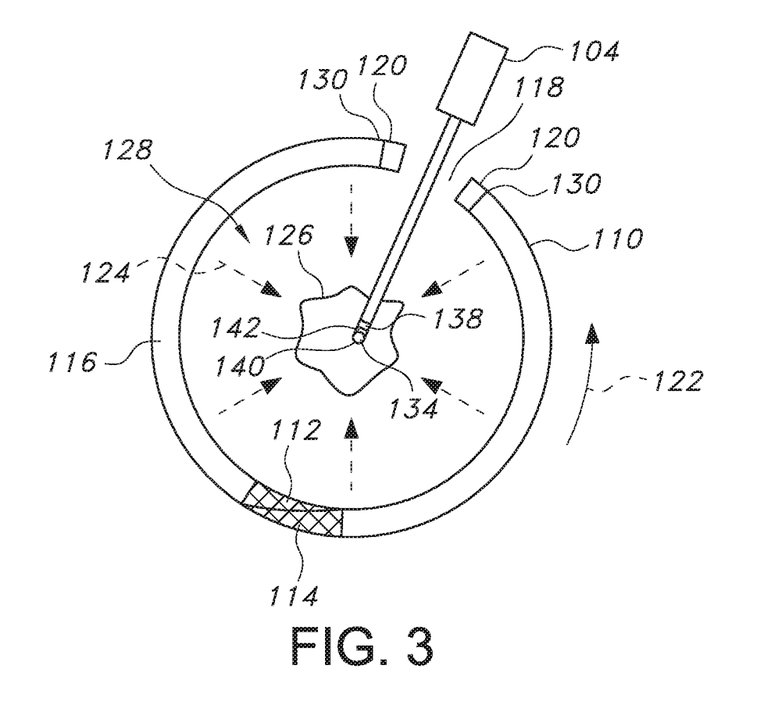
FIG. 3 is a cross-sectional view of the system of FIG. 2 in use

As shown in more detail in the cross-section view of FIG. 3, the device 110 can surround an area or volume of tissue 128 to stabilize the area or volume of tissue 128 during the delivery of radiofrequency energy via a radiofrequency ablation probe 104. The energy can be delivered through an active electrode 134 present at the tip 140 of the probe 104. As a result of the delivery of radiofrequency energy to the area or volume of tissue 128, a lesion 126 can be formed, where the lesion can reduce the level of pain experienced by the patient and originating from the area or volume of tissue 128. Specifically, the device 110 can transfer the elastic tension 122 in the wrap, band, brace, etc. into a compressive force 124 localized around the lesion 126 to increase the contact area and force between the tip 140 of the radiofrequency ablation probe 104 and the area or volume of tissue 128, which allows for better temperature feedback control via the thermocouple 142 present at the tip 140 of the radiofrequency ablation probe 104, as well as improved and consistent delivery of the radiofrequency ablation energy in terms of power levels. Further, the stiffening element 120 disposed about the perimeter 130 of the opening 118 helps transfer the elastic tension 122 in the elastic portion 116 of the device 110 into a compressive force 124.

In addition, the radiofrequency ablation probe 104 can include a radiopaque band 138 near its tip 140 in order to facilitate the insertion of the radiofrequency ablation probe 104 in the correct location since the device 110 may block the user's view in positioning the radiofrequency ablation probe 104 once the probe 104 is inserted through the opening 118. Any suitable radiopaque marker can be used to form the band 138. An example of a suitable radiopaque material that may be used to impart the desired radiopacity is radiopaque ink with tungsten that is pad printed onto the probe 104. The addition of a silver solder band is another technique that may be used to impart the desired radiopacity to the probe 104. Other suitable materials include, but are not limited to, high density metals such as platinum, iridium, gold, silver, tantalum or their alloys, or radiopaque polymeric compounds. Such materials are highly visible under fluoroscopic illumination and are therefore visible even at minimal thicknesses. Regardless of the radiopaque marker utilized on the radiopaque band 138, the band 138 can be used in conjunction with an x-ray, fluoroscopy, or ultrasound device in order to visualize the exact location of the probe 104 during insertion of the probe 104 into the area or volume of tissue 128.

Figure 4:
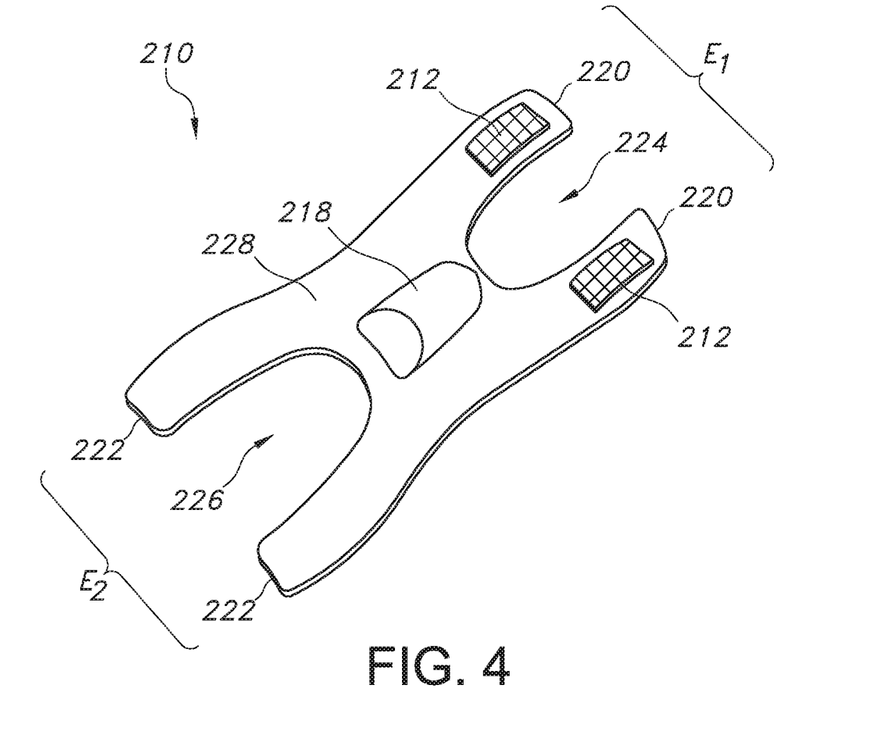
FIG. 4 is a perspective view of another embodiment of a tissue stability device as contemplated by the present invention
Figure 5:
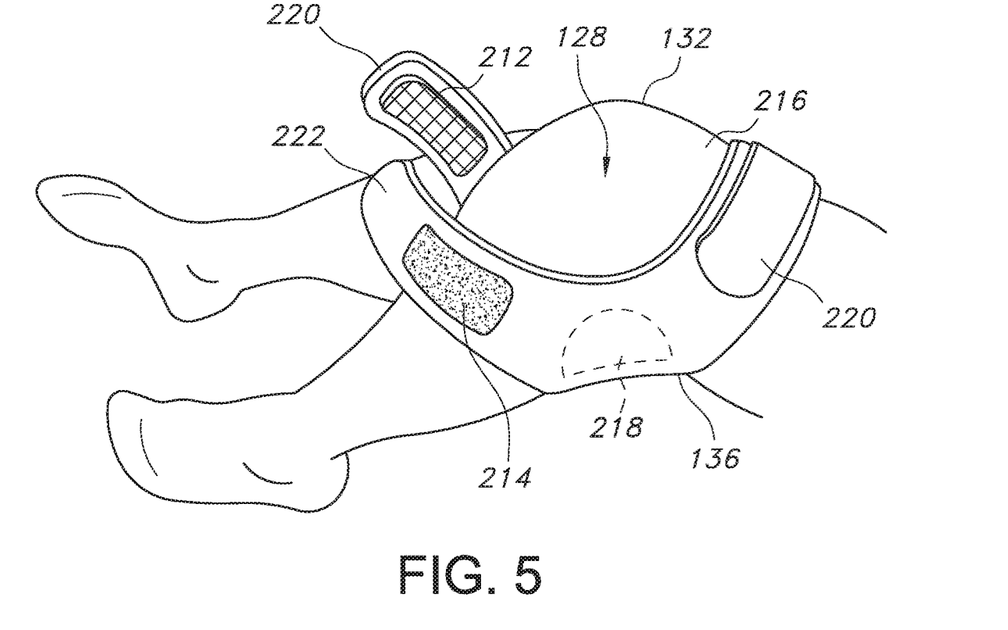
FIG. 5 is a perspective view of the device of FIG. 4 as it is being wrapped around a patient's knee.
Figure 6:
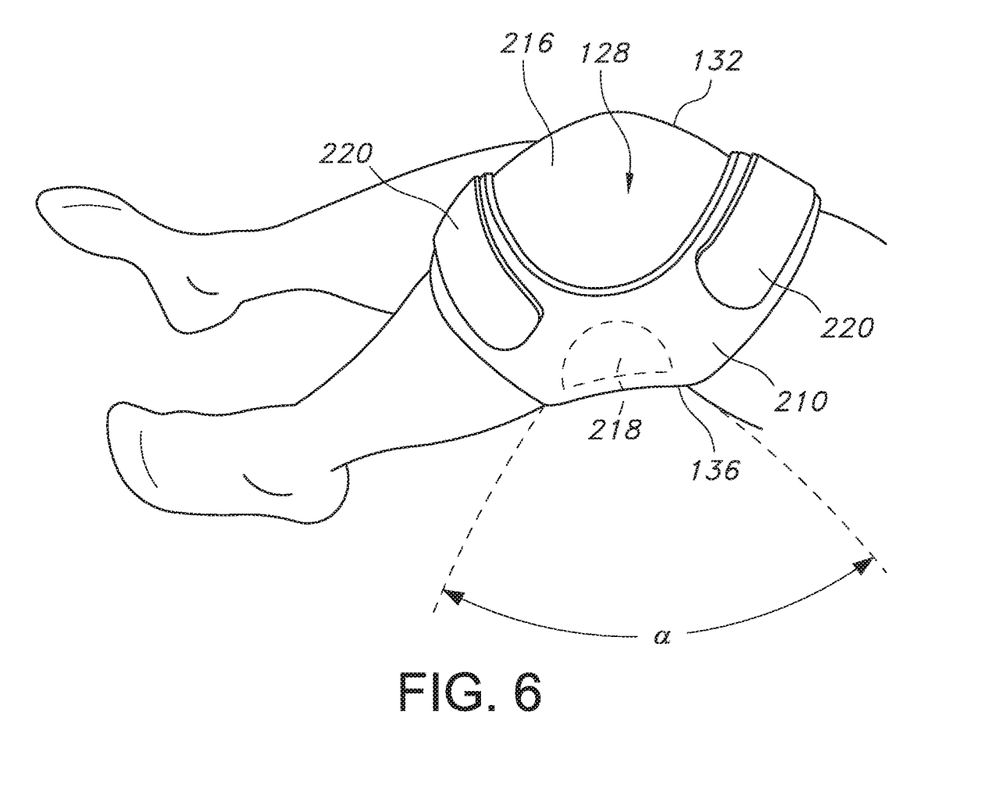
FIG. 6 is a perspective view of the device of FIG. 4 after it has been secured about the patient's knee.

Referring now to FIGS. 4 to 6, another embodiment of a device 210 contemplated for use in the system 100 of FIG. 2 is shown. FIG. 4 shows the device 210 before it is secured about an appendage (e.g., leg, knee, arm, elbow, etc.) of patient, while FIG. 5 shows the device 210 as it is being secured about a knee 132 of a patient. Further, FIG. 6 shows the device 210 after it has been secured about the knee 132 of the patient. As shown in FIG. 4, the device 210, which can be formed from any of the materials discussed above with respect to the device 110, includes two extensions 220 that define a u-shaped cutout 224 at one end E1 of the device 210 and two opposing extensions 222 that define a second u-shaped cutout 226 at an opposing end E2 of the device 210. The device 210 can also include a stabilizing bolster 218 that can be present on a skin-contacting surface 228 of the device 210. As shown in FIGS. 5 and 6, when the device 210 is secured about a knee 132 of a patient via hooks 212, loops 214, or any other suitable fastening means to form an opening 216 in the device 210, the stabilizing bolster 210 can be placed or located near the back 136 of the knee 132. The presence of the stabilizing bolster 210 at the back 136 of the knee 132 can help maintain the knee 132 in the proper position during the delivery of radiofrequency ablation energy to the area or volume of tissue 128 via the probe 104 (see FIGS. 2-3). For instance, the stabilizing bolster 210 can immobilize the knee and maintain a bend in the knee of the patient, where the bend has an angle α ranging from about 70° to 180°. For example, the angle α can range from about 80° to about 175°, such as from about 90° to about 170°, such as from about 100° to about 150°. The stabilizing bolster can be formed of any material, such as a foam, gauze, fabric, etc. provided that the material has sufficient rigidity to avoid substantial deformation under placement pressure (i.e., during initial placement, adjustment and RF procedure). The stabilizing bolster may be configured to be pre-set or predetermined. Alternatively and/or additionally, the stabilizing bolster may be configured to be adjustable through mechanisms including, but not limited to, modular sections or segments, ratchet systems, mechanical fastening systems that rely on friction, clamps or interference fits (e.g., protractor or angle measurement devices) and/or hook and loop fastening systems or combinations thereof.

In addition, although not shown, the device 210 can include a stiffening element that can surround opening 216, where the stiffening element can help to transfer radial compression to the area or volume of tissue 128 that is being treated, which can increase tissue stability at the ablation site. As discussed above with respect to the device 110, the stiffening element can be formed from a rigid ring of a plastic material, a metal material, or a composite material and can be disposed on a surface of the device 210. As noted above, stiffening element may be radiopaque. By making the stiffening element radiopaque, it is generally believed to make it easier to co-locate the probe after placement relative to the compression device. Any suitable radiopaque marker can be used to render all (or only one or more portions) of the stiffening element radiopaque. An example of a suitable radiopaque material that may be used to impart the desired radiopacity is radiopaque ink with tungsten that is pad printed onto the stiffening element. Other suitable materials include, but are not limited to, high density metals such as platinum, iridium, gold, silver, tantalum or their alloys, or radiopaque polymeric compounds. Such materials are highly visible under fluoroscopic illumination and are therefore visible even at minimal thicknesses. Regardless of the radiopaque marker utilized on the stiffening element, the stiffening element can be used in conjunction with an x-ray, fluoroscopy, or ultrasound device in order to help visualize and co-locate a probe (desirably a radiopaque probe) during insertion of the probe into the area or volume of tissue.

The present invention may be better understood by reference to the following examples.

EXAMPLE 1

Figure 7:
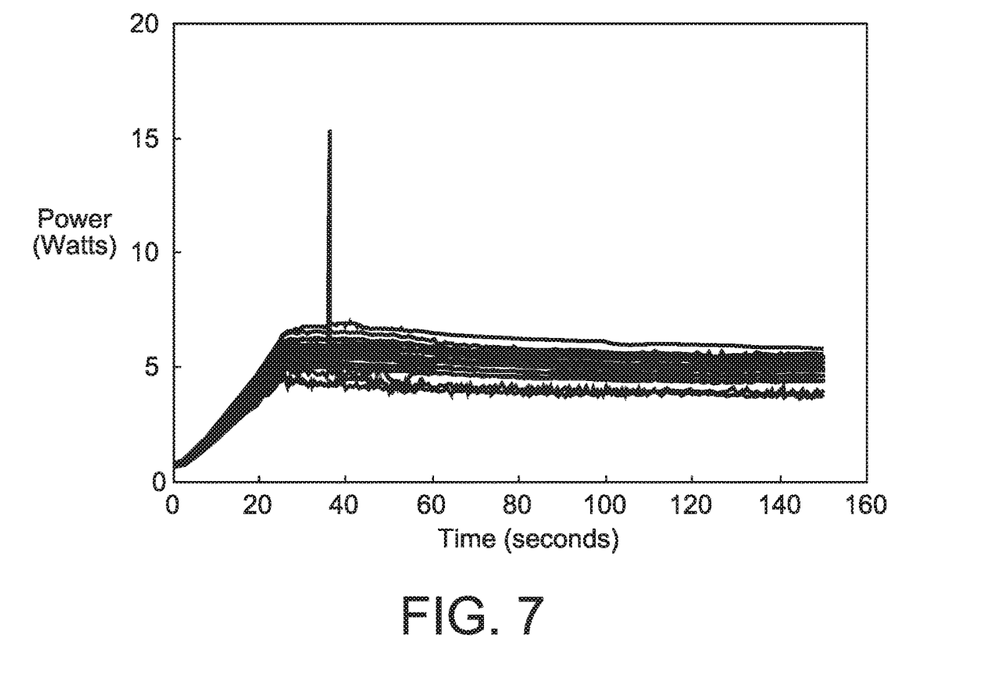
FIG. 7 is a graph showing the power response during ablation when the device of the present device was utilized to stabilize the area surrounding the tissue to be treated.
Figure 8:
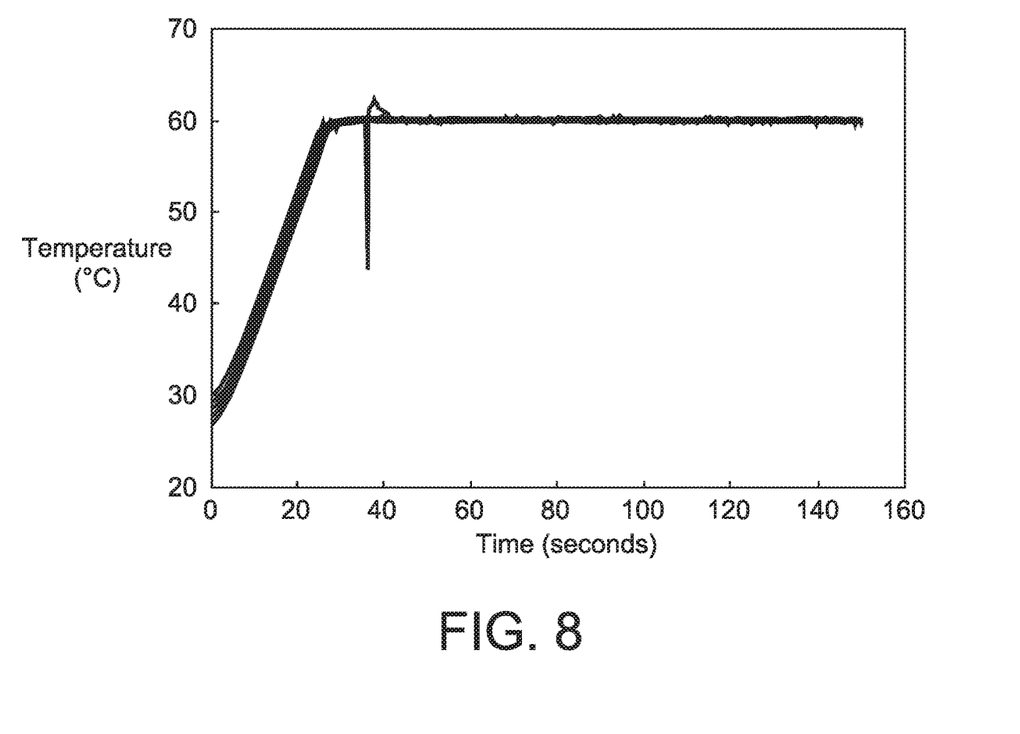
FIG. 8 is a graph showing the temperature response during ablation when the device of the present device was utilized to stabilize the area surrounding the tissue to be treated.
Figure 9:
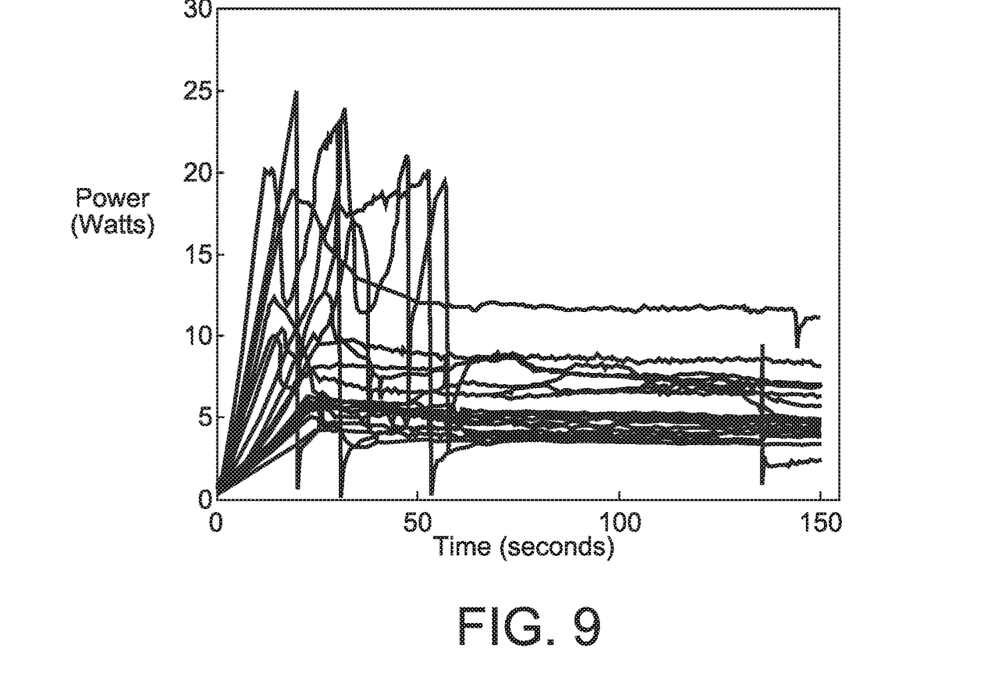
FIG. 9 is a graph showing the power response during ablation when the device of the present device was not utilized to stabilize the area surrounding the tissue to be treated.
Figure 10:
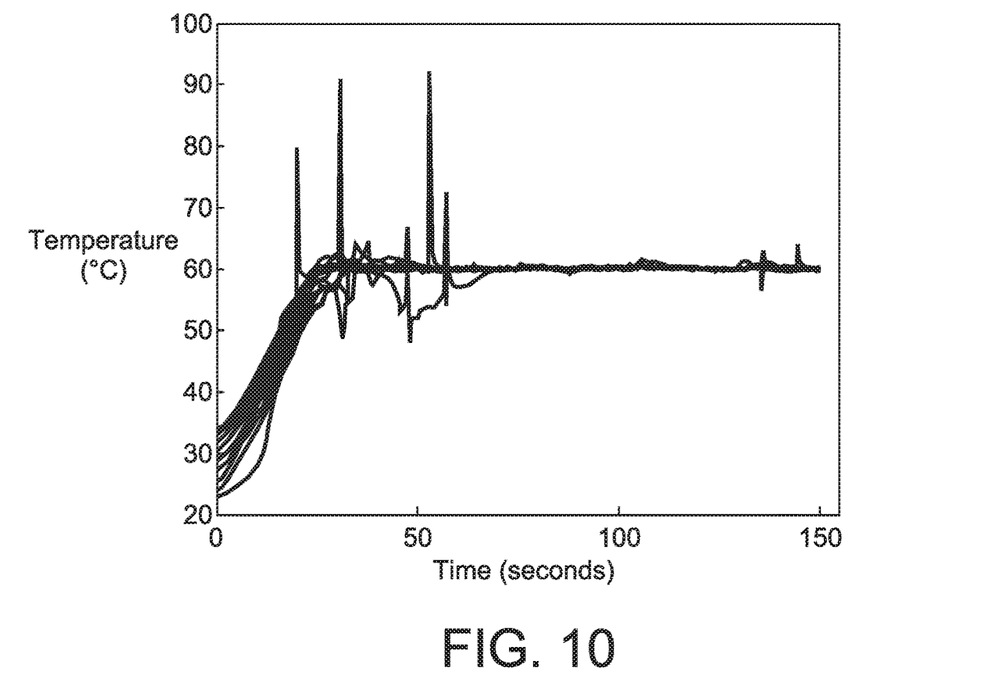
FIG. 10 is a graph showing the temperature response during ablation when the device of the present device was not utilized to stabilize the area surrounding the tissue to be treated.

In Example 1, the power and temperature responses versus time were measured during a radiofrequency ablation procedure that utilized the tissue stabilizing device of the present invention and during a radiofrequency ablation procedure that did not utilize the tissue stabilizing device of the present invention. The radiofrequency ablation procedure utilized a Radiofrequency Generator (also referred to as a PMG), in this case PMG Version 4.1.1, available from Halyard Health, Inc. of Alpharetta, Georgia 30004. The probe used was CRP-17-75 (75 mm length, 17 gauge, 4 mm active tip—cooled probe) used in combination with an introducer Model CRI-17-75-4 (75 mm length, 17 gauge) and Model PPU peristaltic pump unit, all available from Halyard Health, Inc. of Alpharetta, Georgia 30004. The cooling fluid was deionized water at approximately room temperature (23° C.). The probe had an integrated temperature sensor/thermocouple located at the distal end of the active tip. The power and temperature were measured by the Radiofrequency Generator and captured by a computer from the RS232 serial communication port of the Radiofrequency Generator. FIG. 7 shows the power response in watts, while FIG. 8 shows the temperature response in degrees Celsius. Next, the power and temperature responses versus time were measured during a radiofrequency ablation procedure that did not utilize the tissue stabilizing device of the present invention. FIG. 9 shows the power response in watts, while FIG. 10 shows the temperature response in degrees Celsius. As shown in a comparison of FIG. 7 with FIG. 9, the power response in FIG. 7 was much more uniform and controlled when the device of the present invention was used to stabilize the area or volume of tissue around the lesion site compared to the power response in FIG. 9 where the device was not utilized. Likewise, as shown in a comparison of FIG. 8 with FIG. 10, the temperature response in FIG. 8 was much more uniform and controlled when the device of the present invention was used to stabilize the area or volume of tissue around the lesion site compared to the temperature response in FIG. 10 where the device was not utilized.

EXAMPLE 2

Figure 11:
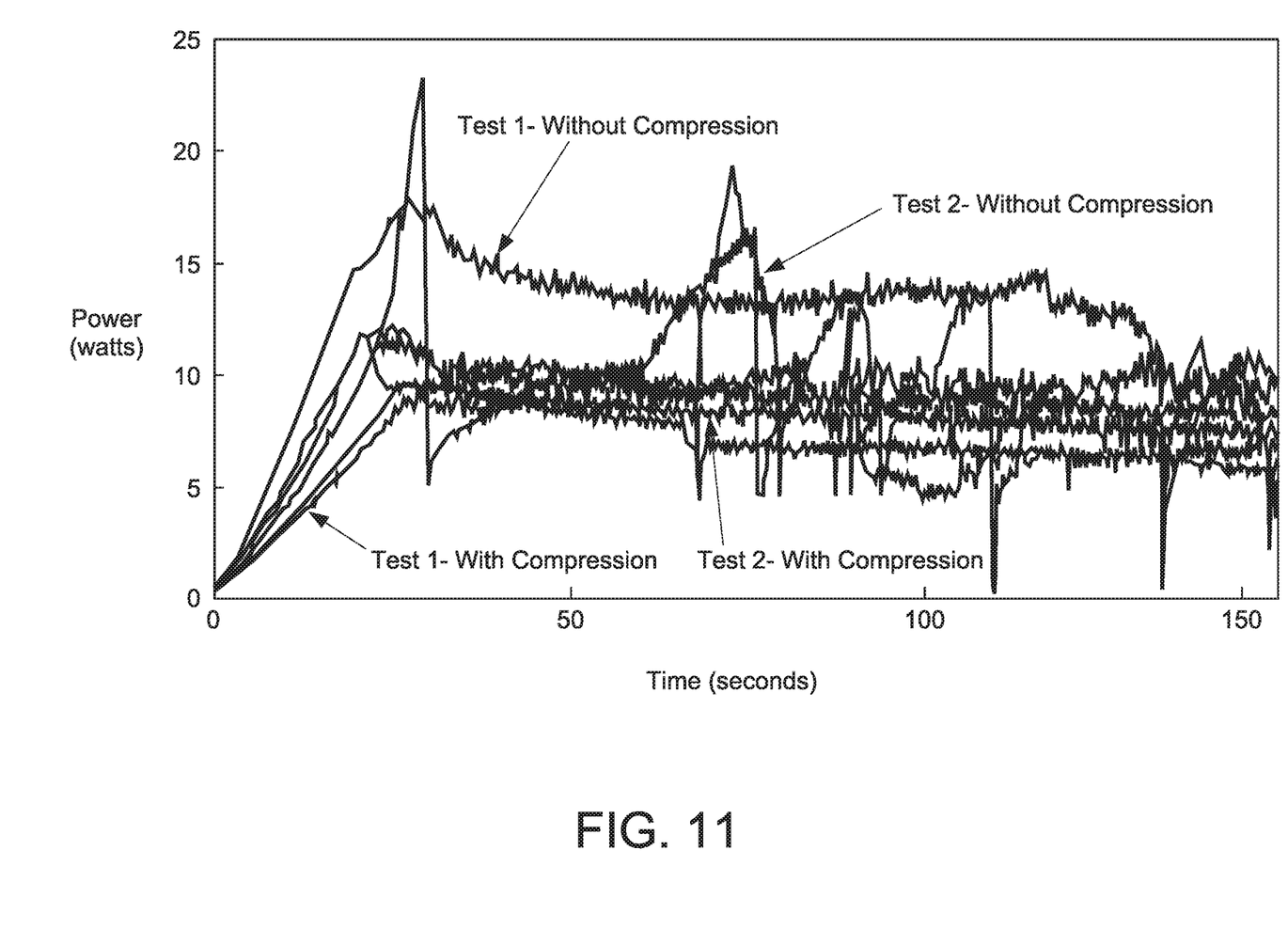
FIG. 11 is a graph comparing the power response during two ablation procedures conducted without utilizing the tissue stabilization device with the power response during two ablation procedures that utilized the tissue stabilization device of the present invention.

Example 2 utilized the same equipment described above for Example 1. In Example 2, the power response versus time were measured during two radiofrequency ablation procedures that utilized the tissue stabilizing device of the present invention and during two radiofrequency ablation procedures that did not utilize the tissue stabilizing device of the present invention. As shown in FIG. 11, the power response during the two ablation procedures that utilized the tissue stabilizing device of the present invention were much more uniform and controlled compared to the power response during the two ablation procedures that did not utilize the tissue stabilizing device of the present invention.

The present invention has been described both in general and in detail by way of examples. These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A system for delivering radiofrequency ablation energy to a volume of tissue, the system comprising:
    a wrap comprising a stiffening element that surrounds an opening in the wrap, wherein the stiffening element transfers radial compression to the volume of tissue to increase stability of the volume of tissue; and
    a radiofrequency ablation probe having an active electrode, wherein the radiofrequency ablation probe is connected to a radiofrequency generator via a lead, wherein the transfer of radial compression to the volume of tissue improves contact between the volume of tissue and the active electrode of the radiofrequency ablation probe.

2. The system of claim 1, wherein the wrap comprises an elastic material and fastening means.

3. The system of claim 1, wherein the opening facilitates insertion of the active electrode of the radiofrequency ablation probe into the volume of tissue and further wherein at least a portion of the stiffening element comprises a radiopaque material.

4. The system of claim 1, wherein the wrap facilitates immobilization of the volume of tissue, wherein the wrap is adjustable to accommodate limb diameters ranging from 8 inches (20.32 centimeters) to 40 inches (101.6 centimeters).

5. The system of claim 4, wherein the volume of tissue is located at a knee of a patient, wherein a bend in the knee of the patient is maintained at an angle ranging from 70° to 180°.

6. The system of claim 1, wherein the radiofrequency ablation probe includes a radiopaque marker adjacent the active electrode.

7. A method of delivering radiofrequency ablation energy to a volume of tissue, the method comprising:
    providing radial compression to the volume of tissue using a wrap secured about the volume of tissue, wherein the wrap has an opening formed therein and comprises a stiffening element surrounding the opening;
    inserting a radiofrequency ablation probe into the volume of tissue through the opening, the radiofrequency ablation probe comprising an active electrode; and
    delivering energy to the volume of tissue through the active electrode of the radiofrequency ablation probe to form a lesion, wherein the radial compression due to the wrap reduces gas buildup at the lesion, wherein the stiffening element transfers radial compression to the volume of tissue, wherein the radial compression increases stability of the volume of tissue, wherein the transfer of radial compression to the volume of tissue improves contact between the volume of tissue and the active electrode of the radiofrequency ablation probe.

8. The method of claim 7, wherein the radiofrequency ablation probe is secured about the volume of tissue via fastening means.

9. The method of claim 7, wherein the volume of tissue is immobilized by the wrap, wherein the wrap is adjustable to accommodate limb diameters ranging from 8 inches (20.32 centimeters) to 40 inches (101.6 centimeters).

10. The method of claim 7, wherein the volume of tissue is located at a knee of a patient, wherein a bend in the knee of the patient is maintained at an angle ranging from 70° to 180°.

11. The method of claim 7, wherein at least a portion of the stiffening element comprises a radiopaque material, wherein the radiopaque material facilitates location of the radiofrequency ablation probe during insertion of the radiofrequency ablation probe into the volume of tissue.

* * * * *